United States Patent [19]

Miller et al.

[11] 4,000,458
[45] Dec. 28, 1976

[54] METHOD FOR THE NONCONTACTING MEASUREMENT OF THE ELECTRICAL CONDUCTIVITY OF A LAMELLA

[75] Inventors: Gabriel Lorimer Miller, Westfield; David Arthur Hall Robinson, Murray Hill, both of N.J.; John Duncan Wiley, Stuttgart, Germany

[73] Assignee: Bell Telephone Laboratories, Incorporated, Murray Hill, N.J.

[22] Filed: Aug. 21, 1975

[21] Appl. No.: 606,365

[52] U.S. Cl. .............................. 324/34 R; 324/40; 324/62
[51] Int. Cl.² ...................................... G01R 33/12
[58] Field of Search ............. 324/34 R, 34 TR, 40, 324/62

[56] References Cited
UNITED STATES PATENTS

| | | | |
|---|---|---|---|
| 3,152,303 | 10/1964 | Lary et al. | 324/40 |
| 3,234,461 | 2/1966 | Trent et al. | 324/62 R |
| 3,544,893 | 12/1970 | Savin et al. | 324/34 R |
| 3,646,436 | 2/1972 | Chan et al. | 324/62 R |

*Primary Examiner*—Robert J. Corcoran
*Attorney, Agent, or Firm*—Allen N. Friedman

[57] ABSTRACT

The electrical conductivity of a lamella of conducting material (e.g., semiconductor wafers or metal films) is measured by introducing the lamella into the oscillatory magnetic field of the inductive element of the L-C tank circuit. The tank circuit is the frequency determining portion of an oscillator which is adjusted, upon sample introduction, to restore the magnitude of oscillation. With suitable choice of circuit parameters, the incremental current in the tank circuit is linearly proportional to the sheet conductivity of the lamella. An exemplary apparatus, operating at approximately 10 MHz with a 1 cm² measurement area exhibited approximately 1% linearity over a 100 to 1 range of conductivity with a resolution of approximately one part in $10^4$ with a limiting sensitivity of $10^{11}$ carriers per square cm.

5 Claims, 5 Drawing Figures

METHOD FOR THE NONCONTACTING MEASUREMENT OF THE ELECTRICAL CONDUCTIVITY OF A LAMELLA

BACKGROUND OF THE INVENTION

1. Field of the Invention

The invention is in the field of electronic solid state device processing, more particularly, semiconductor wafer or metal thin film conductivity measurement.

2. Brief Description of the Prior Art

The ability to rapidly and accurately measure the electric conductivity of thin flat samples (lamellae) is of critical importance in many aspects of solid state device processing. Such measurements are essential parts of the classification of semiconductor substrate materials prior to processing, to the monitoring of dopant diffusions and the monitoring of metal thin film depositions. The most widely used measurement technique is the four point probe method. However this method has several limitations, for example, it is difficult to interpret the results of such a measurement made on high resistivity semiconductor samples. In addition the probe causes localized surface damage at the point of contact. Such surface damage becomes more and more detrimental as the element size of microminiature circuits becomes smaller.

Various noncontacting techniques for the measurement of electrical conductivity have been developed in an effort to avoid the limitations of the four point probe technique. These methods generally involve the interaction of the sample being measured with high frequency excitations. Exemplary techniques of this class include: microwave transmission measurements through a semiconductor slab placed in a waveguide (H. Jacobs et al. *Proceedings of the IRE*, 49 (1961) 928); reflection of an RF signal from a coaxial line terminated by the sample (C. A. Bryant et al. *Reviews of Scientific Instruments*, 26 (1965)1614); and capacitive coupling and inductive coupling to a resonant circuit (N. Nuyamoto et al. *Reviews of Scientific Instruments*, 38 (1967) 360; J. C. Brice et al. *Journal of Scientific Instruments*, 38 (1961) 307). Such methods typically produce nonlinear output signals which require calibration over the range of use and comparison of the measurement signals to the calibration curve. In addition, such measurements have typically made use of some relatively ill defined measurement volume (e.g., approximately hemispherical), which may be quite satisfactory for the measurement of uniformly conductive samples, however, increase the complexity of analysis of measurement results for nonuniform samples (e.g., diffused layers in semiconductors).

SUMMARY OF THE INVENTION

A noncontacting technique has been developed for the measurement of the electrical conductivity of thin flat samples (lamellae) such as semiconductor wafers or metal thin films. This technique produces a highly linear output signal and measures the conducting carriers uniformly through the thickness of the material. This high degree of linearity together with the ability to control the level of the output signal can be used to produce the direct reading of conductivity on, for example, a digital voltmeter. This capability makes the inventive technique particularly attractive for production line monitoring of diffusions and depositions in substrates in electronic device processing.

In the inventive technique the sample is introduced into the magnetic field of the inductive element of a resonant circuit and the drive current of the resonator is adjusted to restore the amplitude of oscillation to the value it had prior to introduction of the sample. If the frequency of oscillation is selected to make skin effect negligible and if the resonator is the frequency determining element of the oscillation circuit, then the incremental current is linearly related to the sheet conductivity of the sample. In exemplary apparatus constructed to illustrate this measurement technique, feedback is used to automatically restore the oscillation amplitude. This exemplary apparatus was linear within approximately 1% over a 100 to 1 range of conductivity with a resolution of approximately one part in $10^4$. The limiting sensitivity of the instrument was $\sim 10^{11}$ carriers per square centimeter.

DETAILED DESCRIPTION OF THE INVENTION

The measurement of the electrical conductivity (or resistivity) of broad thin solid bodies is of major importance in many facets of solid state device processing. For example it is usually necessary to classify semiconductor substrates prior to processing to make sure that the conductivity of the substrates is either less than a specified low value or within some narrow conductivity range. During processing it is usually necessary to monitor diffusion steps to determine when the conductivity of the diffused wafers has increased or decreased to some conductivity with a narrow range, which is related to the desired dopant concentration and diffusion depth. Many diffusions are caused to take place through apertured masking layers. In such cases a blank wafer can be included for monitoring purposes. Most solid state device processes includes the deposition of metal layers for the production of electrical contact between devices in an integrated circuit or between the circuit and external circuitry. In such cases the layer must be thicker than some minimum thickness, in order to provide sufficient conductivity, but not unnecessarily thick, so as to be wasteful of precious metals such as gold and platinum. Thus, the monitoring of metal layer thickness becomes an important manufacturing process step.

The most widely used method for making the required conductivity measurements is the four point probe technique. However, for low conductivity semiconductor materials with large band gaps these methods are exceedingly difficult because the contacts between the wafer being measured and the contacting elements of the four point probe tend to be rectifying. Also, some diffusions take place through glassy layers making it difficult to contact the underlying semiconductor. The four point probe, since it directly contacts the material, produces localized damage. The damaged area can be made unsuitable for use, particularly for devices with small element size. The above considerations make the development of a noncontacting method particularly desirable.

Figure 1:
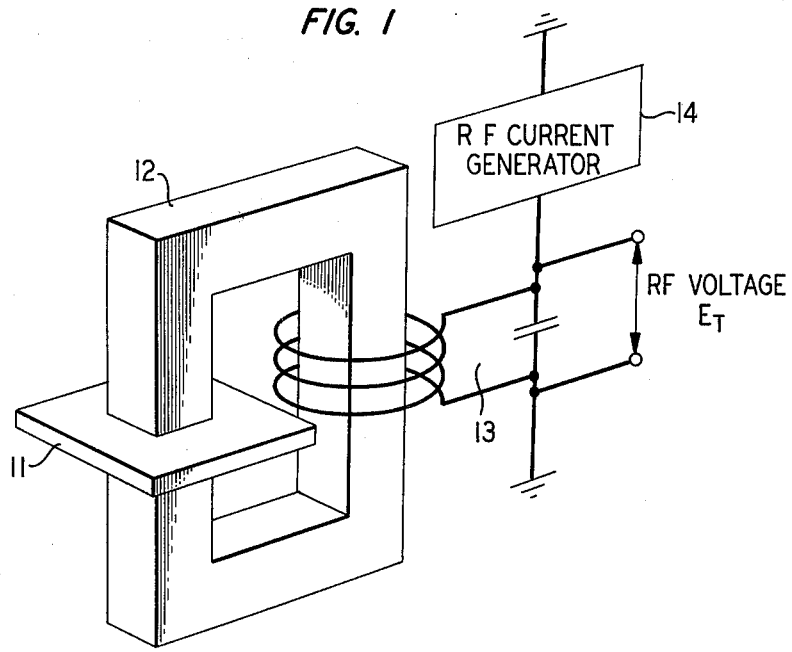
FIG. 1 is a schematic representation of the basic elements of a device for the practice of the claimed method.

The herein disclosed noncontacting method for the electrical conductivity measurement of conducting lamellae produces a highly linear output. This makes possible, for example, single point calibration and, with the availability of signal level adjustment, the direct reading of conductivity on a digital voltmeter. The measurement method can be understood with reference to FIG. 1 which shows a conductive lamella 11 magnetically coupled by means of a ferrite core 12 to an L-C resonant tank circuit 13. This parallel resonant circuit 13 is driven by an RF current generator 14. Operation of the measurement method depends upon the fact that eddy current absorption in the conducting lamella 11 produces an increase in the loss of the resonant circuit 13. It has been determined that, if the resonant circuit 13 determines the frequency of oscillation so that the frequency shifts with the loading of the circuit 13 and the frequency of oscillation is selected such that skin effect in the lamella is negligible and the current generator 14 is adjusted to restore the amplitude of oscillation after sample insertion, then the incremental current flowing from the current generator 14 into the resonant circuit 13 is linearly related to the product of the bulk conductivity of the conducting material multiplied by the thickness of the material. This product is sometimes referred to as the sheet conductivity of the sample and is related to the product of the number of carriers in the measured volume and the carrier mobility. In the frequency regime of negligible skin effect, the product of conductivity times thickness generalizes to the integral of the conductivity through the thickness so that data for nonuniform samples can be easily analyzed. The basic relationship which governs the measurement process is $$I = K(E/n^2)\sigma t \qquad \text{(Eq. 1)}$$

In this equation $I$, assuming no circuit losses except those in the lamella, is the oscillating frequency current flowing into the resonator, $K$, is a constant involving the magnetic coupling between the inductor core and the lamella, $E$, is the oscillating frequency voltage across the resonator, $n$, is the number of turns in the inductor, $\sigma$, is the electrical conductivity of the lamella material and, $t$ is the thickness of the lamella. If other circuit losses are considered the resonator losses can be represented as a parallel loss resistance $R_p$. This parallel loss resistance consists of two parts, namely, the tank circuit loss itself, $R_T$ and the reflected loss due to eddy currents in the lamella, $R_S$. These combine as $$\frac{1}{R_p} = \frac{1}{R_T} + \frac{1}{R_S}. \qquad \text{(Eq. 2)}$$

However the current generator 14 is adjusted after insertion of the sample to maintain the level of oscillation (i.e., the voltage across the resonant circuit 13) at a constant value. Thus, $$IR_p = \text{const.} \qquad \text{(Eq. 3)}$$

or $$I \alpha \frac{1}{R_p}. \qquad \text{(Eq. 4)}$$

With no semiconductor loading the value of $I$ has its minimum value, $I_o$, which corresponds to $R_p = R_T$. Consequently equations 2 and 4 yield $$(I - I_o) \alpha \text{ to } \frac{1}{R_S}. \qquad \text{(Eq. 5)}$$

However $1/R_S$ is proportional to the sheet conductivity of the sample thus $$(I - I_o) \alpha \sigma T \qquad \text{(Eq. 6)}$$

This is the result used to determine the sample conductivity, $\sigma$. In apparatus used in this method a "zero" control can be included to balance out $I_o$ in the absence of any sample so that only the incremental current appears as an output. In addition a simple electronic technique is available to remove the dependence on sample thickness, $t$, by dividing by the thickness.

EXEMPLARY MEASUREMENT APPARATUS

Figure 2:
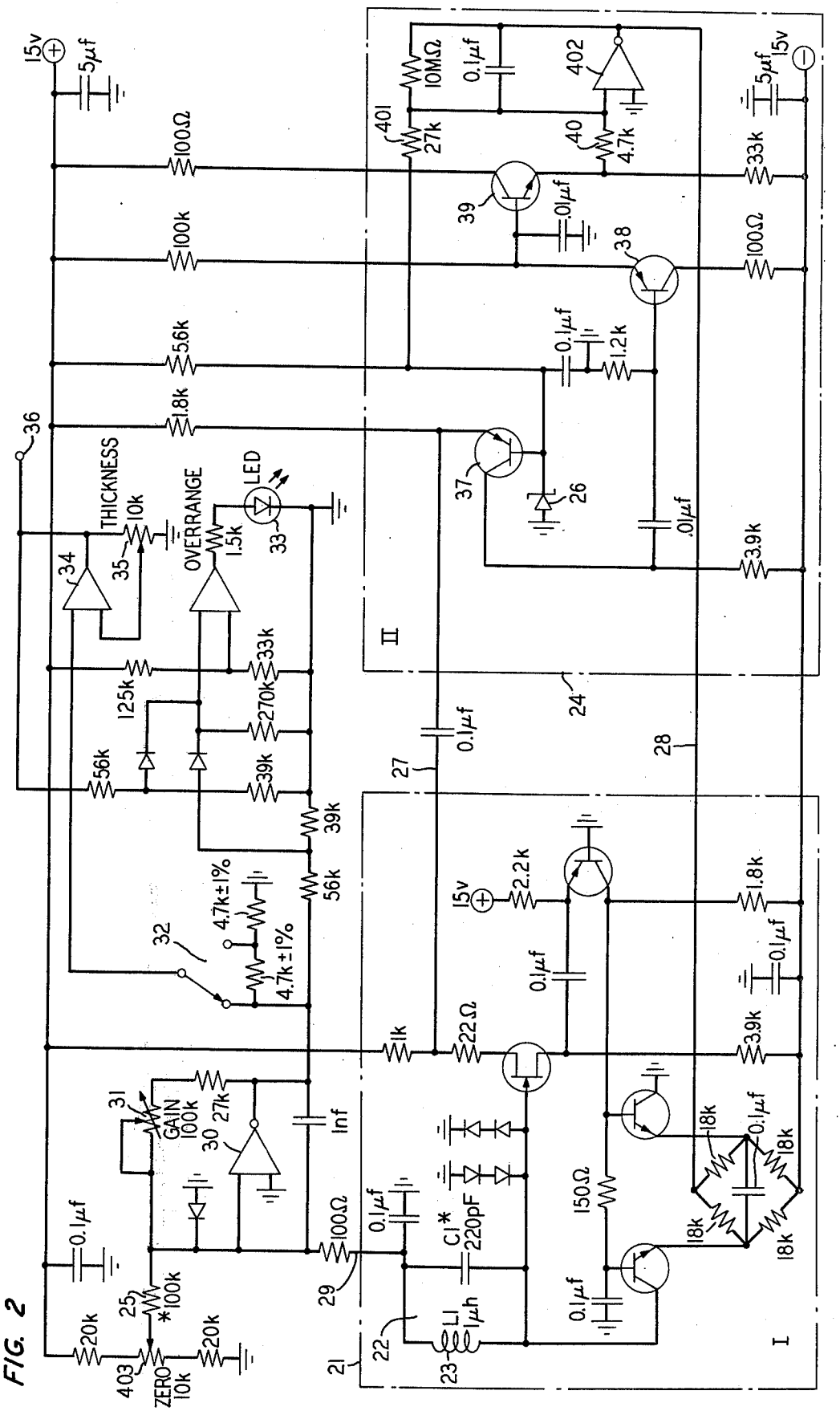
FIG. 2 is a circuit diagram of an exemplary network developed for the practice of the claimed process.

FIG. 2 shows the circuit diagram of an exemplary circuit developed and constructed for the practice of the inventive method. Unless otherwise specified the resistors and ¼ watt and ±5%. The diodes are 1N4154, the NPN transistors are 2N3904, the PNP transistors are 2N3906, the FET's are 2N4393 and the differential amplifiers are high gain (~ 10⁵ at DC, unity at 1 MHz) units suitable for use as operational amplifiers (Type 741). Box I outlined by dashed line 21 includes the resonant tank circuit 22 and the several transistors which form the RF current generator. These elements are arranged to form an amplitude controllable marginal oscillator whose frequency of oscillation is determined by the tank circuit 22. For conductivity measurement, the sample to be measured is magnetically coupled to the inductor 23. A description of the operation of this type of oscillator can be found in *Journal of Scientific Instruments*, 36 (1959) 481. A feature of the oscillator design of FIG. 2 is that the average DC current flowing to ground on the grounded side of the tank circuit 22 is an accurate measure of the magnitude of the oscillation frequency drive current.

The magnitude of the oscillation of the tank circuit 22 is automatically adjusted by feedback through the stabilization circuitry of Box II outlined by dashed line 24. The level of oscillation at the collector of transistor 37 is sensed by the temperature compensated peak rectifier formed by transistors 38 and 39, resulting in a corresponding negative voltage at the emitter of 39. The error amplifier 402 then senses the difference between the resulting current flowing in resistor 40 and the reference current flowing in resistor 401. The stabilization reference is an 8 volt zener diode 26. The tank circuit oscillation amplitude is thereby sensed through lead 27 and the feedback control is supplied by lead 28. The average DC tank circuit current is measured at lead 29 by the action of amplifier 30. The output circuitry includes a gain control pot 31, a range switch 32 and an overrange indicator lamp 33, which lights to indicate the presence of a sample whose conductivity is above the two decade range of the instrument. Amplifier 34 and a precision ten turn potentiometer 35 are arranged so as to accomplish the division of the thickness of the material prior to extraction of the conductivity signal in the output port 36. The gain is adjusted so that potentiometer 35 reads directly in convenient units of sample thichness. The components labeled with an asterisk have values that are selected depending upon the particular choice of input tank circuit, $L_1C_1$. The values indicated are those for an instrument reading out at one volt per mho-cm$^{-1}$, oscillating at approximately 10MHz, employing a gap of 0.025 inches between the two halves of the inductor 23, and measuring sample conductivities in the range ~.05 to ~10 mho-cm$^{-1}$.

Figure 3:
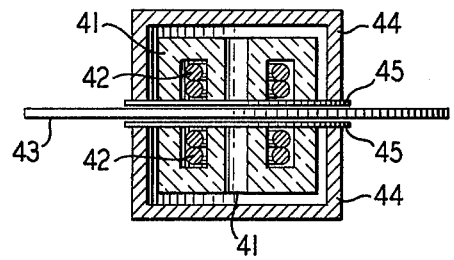
FIG. 3 is an elevational view in section of an exemplary inductor with sample.

The design of the inductor is illustrated in FIG. 3. In order to produce tight-coupling between the RF magnetic field and the sample to be measured, the inductor core design was chosen to be a split high Q ferrite cup core 41 with two turns in each half, resulting in a total inductance of approximately 1μh. The cores employed are characterized by a permeability of ~100 and a Q of ~100 at the 10MHz oscillation frequency. The number of turns 42 can be changed to 20 or 200 etc. to achieve corresponding $10^2$ and $10^4$ range scaling as indicated by the $1/n^2$ dependence of Equation 1. If $C_1$ remains unchanged the attendant reduction of oscillation frequency helps to satisfy the skin effect criterion for the measurement of higher conductivity samples 43.

Figure 4:
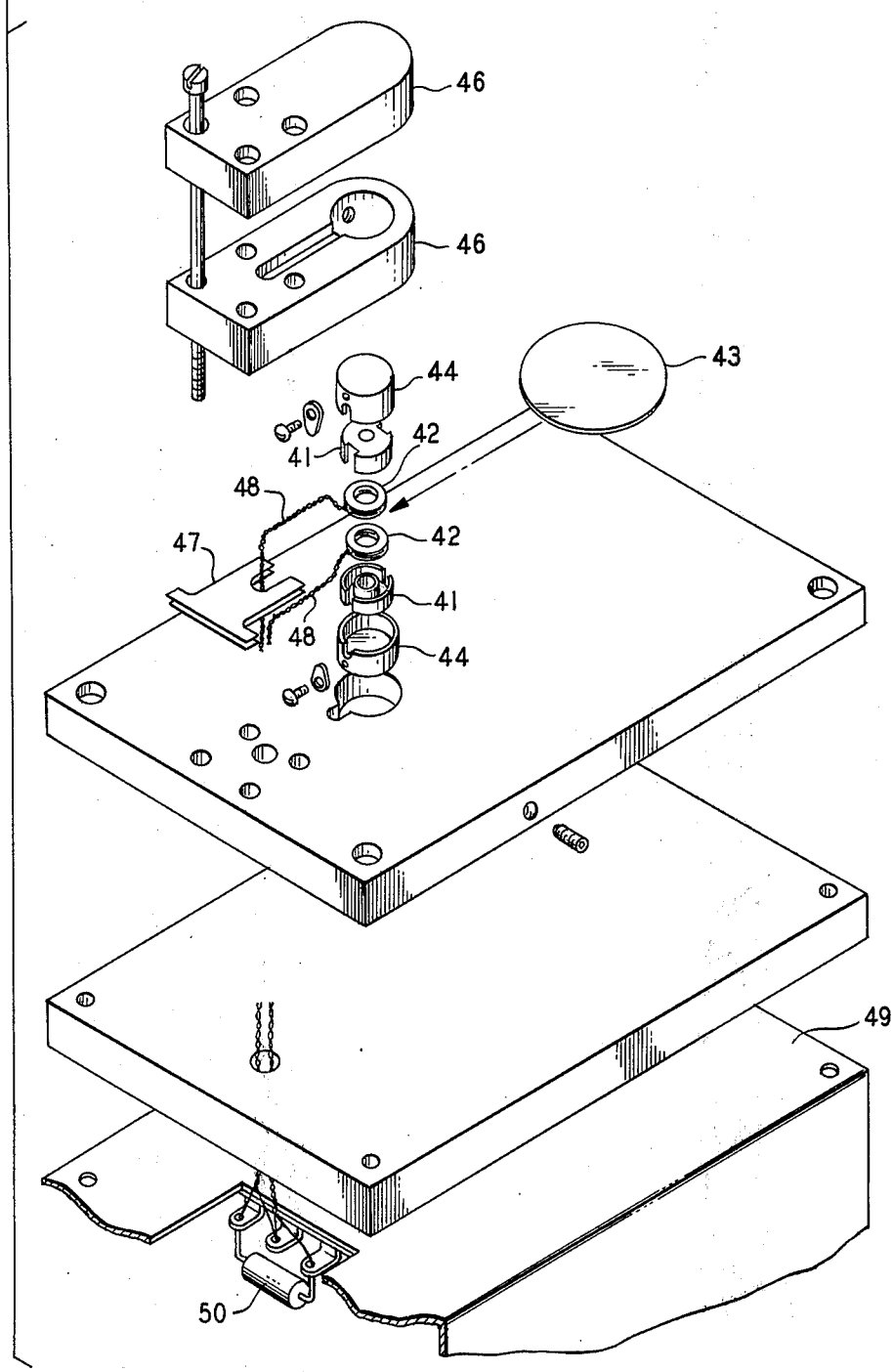
FIG. 4 is an exploded perspective view of the mechanical parts of an exemplary apparatus developed for the practice of a claimed process.

The inductor design also includes seamless aluminum cups 44 which reduce the fringing field and maintain the measurement area precisely and exclusively as the region between the opposing faces of the two core halves. Capacitive coupling to the sample 43 is minimized by the inclusion of an electrostatic shield 45 over the faces of the cores 41. The shield used was an electrically conductive paper (available from Western Union Corp. as TELEDELTOS paper). The mechanical design of the sample measuring head of the constructed instrument is illustrated in exploded view, in FIG. 4. The cup cores 41, the windings 42 and aluminum cups 44 are mounted in polymethylmethacrylate holders 46. The holders 46 are bolted onto the base such that shims 47 can be inserted to adjust the gap between the cores to accommodate various sample 43 thicknesses. The leads 48 from the inductor are shielded and lead downward into case 49 containing the electronic circuitry and connected to the tank circuit capacitor 50. Similar instruments for the measurement of higher conductivity semiconductor wafers (i.e., in the 5 mho-cm$^{-1}$ to $10^3$ mho-cm$^{-1}$ range) can be constructed with 20 turns on each side of the cup core. The operating frequency of such instruments is approximately $10^6$Hz. For the measurement of metal films up to 5 micrometers thick, cup cores with $10^3$ turns on each side, together with a 0.01μ f capacitor, produces an instrument oscillating at approximately $10^4$Hz. Resistor 25 should be selected to give an overall zero reading near the center of the zeroing potentiometer 403.

Figure 5:
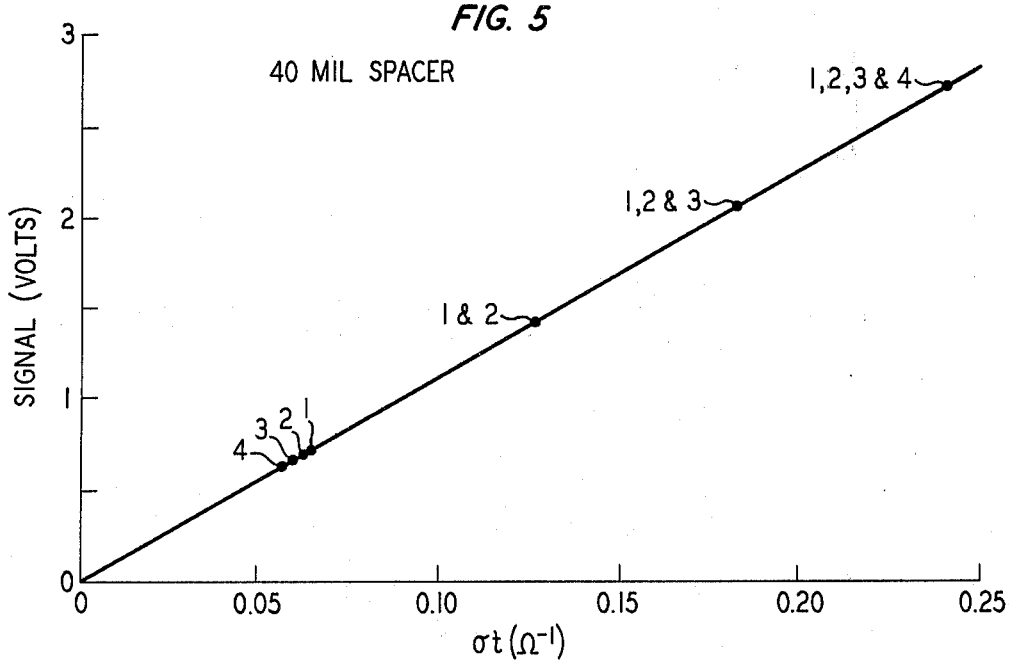
FIG. 5 is a curve of sheet conductivity (ordinate) vs output signal (abscissa) illustrating the linearity of the inventive method.

The linearity of the measurement method as embodied in the above described instrument and the suitability of the method for the measurement of multilayer samples was shown by the following experiment: four slices of semiconductor were measured separately and then superimposed in various combinations. The results of these measurements are illustrated in FIG. 5. Measurements such as these have demonstrated that the instrument response is linear over the entire range to approximately 1%. The various level adjustments were used to produce a signal which read directly in mho-cm$^{-1}$ on a digital voltmeter. The unit was calibrated at one point by a sample of conductivity near the high end of the conductivity range. The limiting performance of the instrument was set by slow long term drifts of the order of a few millivolts per hour corresponding to a few parts in $10^4$ of the system full scale output of approximately 10 volts. The readings were stable and reproducible to this accuracy. Subsequent analysis of the circuit indicated that it may be possible to reduce these drifts by operating at higher oscillator drive levels and eliminating the amplification at the output of the tank circuit 22 (amplifier 30).

Although the above described circuit employed a parallel resonant circuit driven by a high impedance source, equivalent realizations employing a series resonant tank circuit are possible.

What is claimed is:

1. Method for the measurement of the electrical conductivity of a lamella comprising
   a. exciting a resonant circuit at a measurement frequency with a source of electrical energy, which resonant circuit includes a capacitor and an inductor,
   b. introducing the lamella into the magnetic field of the inductor and
   c. deriving an output signal related to the electrical conductivity of the lamella
   characterized in that
   1. the resonant circuit is the principal determinent of the measurement frequency,
      2. the lamella is introduced into the magnetic field of the inductor such that the magnetic field is essentially uniform through the thickness of the lamella,
      3. the output signal is derived by adjusting the source of electrical energy to restore the measurement frequency voltage across the inductor to its value prior to introduction of the lamella, and measuring the incremental measurement frequency current through the inductor.

2. A method of claim 1 in which the measurement of the incremental measurement frequency current includes electronically dividing by the thickness of the lamella.

3. A method of claim 1 adapted for measurement of semiconductor wafers in the conductivity range 0.05 mho-cm$^{-1}$ to 10 mho-cm$^{-1}$ wherein the measurement frequency is approximately $10^7$ Hertz.

4. A method of claim 1 adapted for measurement of semiconductor wafers in the conductivity range 5 mho-cm$^{-1}$ to $10^3$ mho-cm$^{-1}$ where the measurement frequency is approximately $10^6$ Hertz.

5. A method of claim 1 adapted for the measurement of metal films up to 5 micrometers thick wherein the measurement frequency is approximately $10^4$ Hertz.

* * * * *